United States Patent [19]
Kim et al.

[11] Patent Number: 5,728,940
[45] Date of Patent: Mar. 17, 1998

[54] LEAKAGE GAS DETECTOR FOR SEMICONDUCTOR DEVICE AND LEAKAGE GAS DETECTING METHOD USING THE SAME

[75] Inventors: Dae-woo Kim; Jae-kyung Lee; Bon-rip Koo; Sang-woon Kim, all of Suwon, Rep. of Korea

[73] Assignee: Samsung Electronics Co., Ltd., Suwon, Rep. of Korea

[21] Appl. No.: 739,729

[22] Filed: Nov. 7, 1996

[30] Foreign Application Priority Data

Nov. 8, 1995 [KR] Rep. of Korea ............ 95-40266

[51] Int. Cl.⁶ ................... G01M 3/18; G01N 31/08
[52] U.S. Cl. ................. 73/40.7; 73/40.5 R; 73/49.3; 73/49.1
[58] Field of Search ................. 73/40.7, 40.5 R, 73/23.36, 23.42, 49.1

[56] References Cited

U.S. PATENT DOCUMENTS

| | | | |
|---|---|---|---|
| 3,069,898 | 12/1962 | Vesper | 73/23 |
| 3,094,862 | 6/1963 | Burk | 73/23 |
| 3,500,028 | 3/1970 | Killian | 235/183 |
| 3,533,218 | 10/1970 | Hunt et al. | 55/386 |
| 3,733,474 | 5/1973 | Edwards et al. | 235/151.35 |
| 3,942,331 | 3/1976 | Newman, Jr. et al. | 62/45 |
| 4,063,310 | 12/1977 | McDonald | 364/900 |
| 4,184,362 | 1/1980 | Standley et al. | 73/40.7 |
| 4,364,261 | 12/1982 | Askwith et al. | 73/40 |
| 4,380,168 | 4/1983 | Ibe | 73/40.5 R |
| 5,384,714 | 1/1995 | Kidd | 364/550 |

*Primary Examiner*—Hezron E. Williams
*Assistant Examiner*—J. David Wiggins
*Attorney, Agent, or Firm*—Jones & Volentine, L.L.P.

[57] ABSTRACT

A leakage gas detector for a semiconductor device includes a plurality of inflow apertures into which leakage gas flows. A detector sequentially detects the leakage gas in each of the inflow apertures via a plurality of valves, so as to leak test each of the plurality of inflow apertures for presence of possible leakage gas. Each of the plurality of valves are connected to corresponding of the plurality of inflow apertures to control the suction of the leakage gas into the detector. A controller selectively opens and closes each of the plurality of valves.

17 Claims, 2 Drawing Sheets

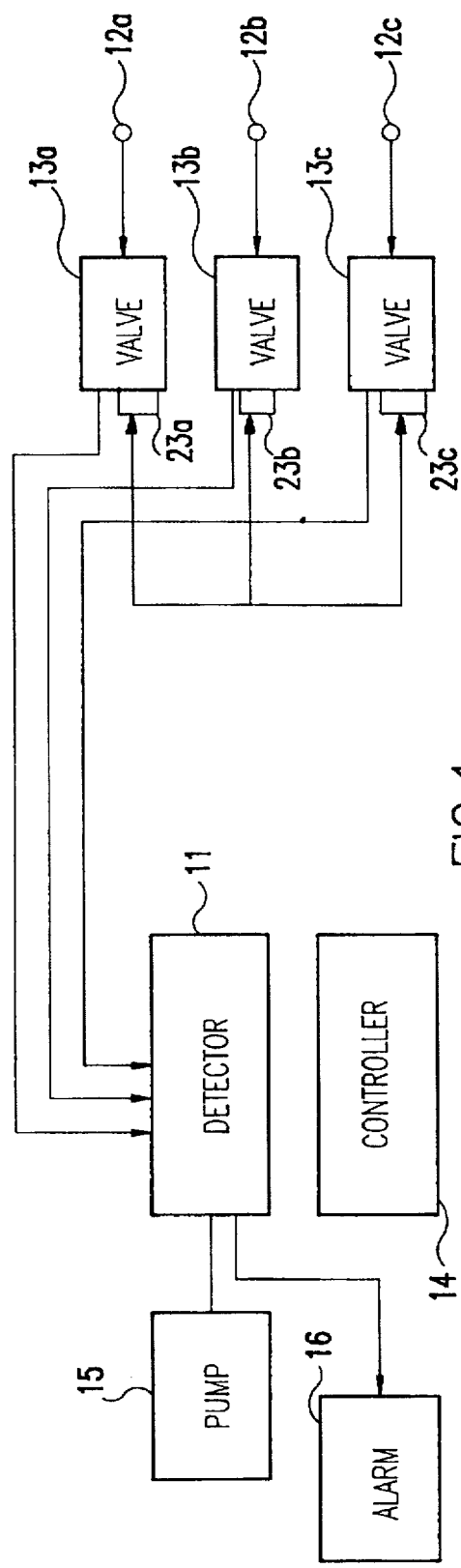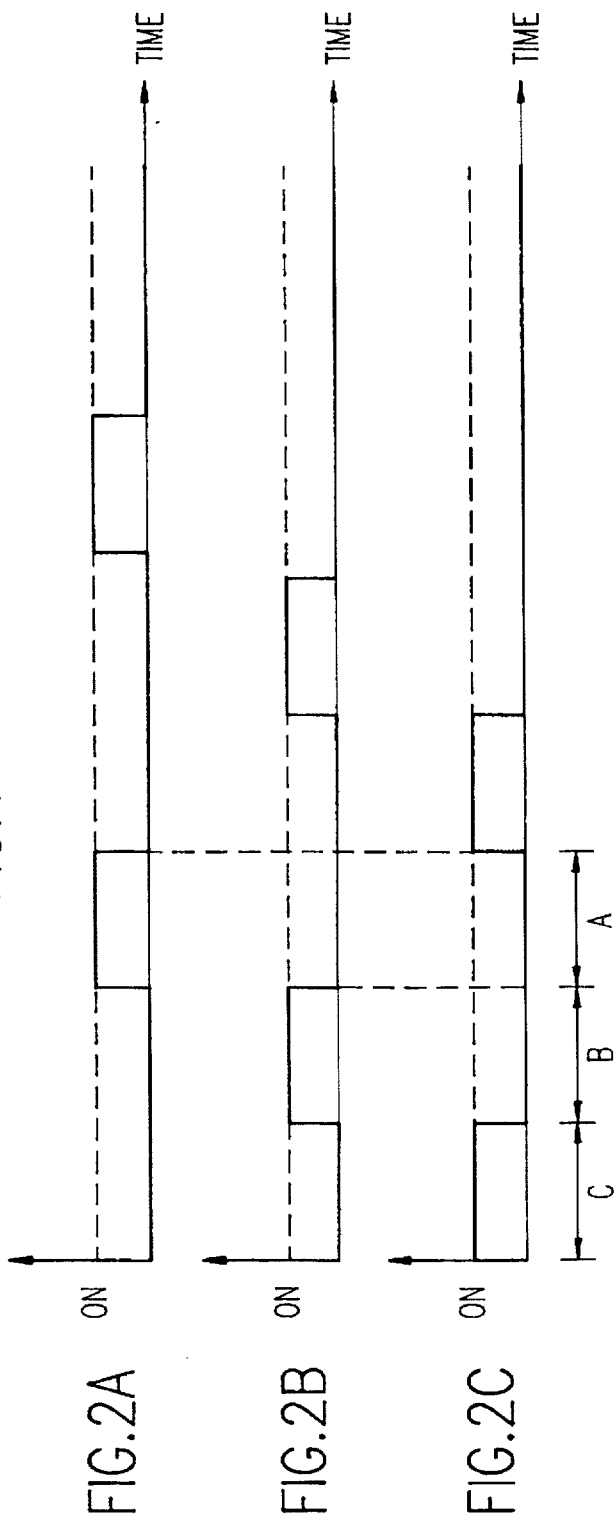

LEAKAGE GAS DETECTOR FOR SEMICONDUCTOR DEVICE AND LEAKAGE GAS DETECTING METHOD USING THE SAME

BACKGROUND OF THE INVENTION

1. Field of the Invention

The present invention relates to a leakage gas detector for a semiconductor device for improving efficiency in the detection of leakage gas by increasing the suction pressure of the leakage gas and a leakage gas detecting method using the same.

2. Background of the Related Art

A predetermined reaction gas is used in the process of manufacturing a semiconductor device, with the gas flowing into a piece of reaction equipment such as a diffusion furnace and deposition apparatus. Any reaction gas that leaks during the inflow thereof contaminates the work place, such that the quality of the product obtained therefrom and yield thereof are decreased, and further, the semiconductor device manufacturing apparatus may be corroded, shortening the life span thereof. Of greater consequence, if oxygen or hydrogen gas is leaked, the reaction equipment may explode. Thus, in order to prevent the above problems, it is necessary to install a leakage gas detector for detecting leakage gas in the semiconductor device manufacturing apparatus.

Generally, a method of detecting leakage gas using the leakage gas detector includes the steps of suctioning the leakage gas into the gas detector, determining whether the amount of leakage gas is over a predetermined value, activating an alarm if the amount of leakage gas is over the predetermined value, and terminating the operation of the reaction equipment in response to a signal generated upon sensing the leakage of gas.

A conventional leakage gas detector has a plurality of inflow apertures into which the leakage gas flows, a plurality of detecting portions which are connected to each inflow aperture for detecting the leakage gas flowing via each inflow aperture, and a suction pump for suctioning the leakage gas through the inflow apertures. However, since the capacity of the suction pump is limited, the suction pressure at each inflow aperture decreases as the number of inflow apertures increases. That is, the amount of leakage gas transferred to each detecting portion is decreased, lowering the efficiency in detecting the leakage gas, and increasing the detection time required. In addition, the alarm signal, signifying gas leakage, may not be generated if the leakage gas is not detected due to a small amount of transferred gas.

Also, if the amount of reaction gas in the diffusion furnace is not sufficient due to the leakage of gas, an intended reaction may not occur. Thus, more gas must be used than is required for the intended reaction.

SUMMARY OF THE INVENTION

Accordingly, it is an object of the present invention to provide a leakage gas detector for a semiconductor device that is capable of effectively detecting the leakage of a reaction gas used in a semiconductor device manufacturing process.

It is another object of the present invention to provide a method for detecting leakage gas where the leakage of a reaction gas used in a semiconductor device manufacturing process can be effectively detected.

To achieve these and other objects, there is provided a leakage gas detector for a semiconductor device comprising: a plurality of inflow apertures into which a leakage gas flows; a detector for detecting the leakage gas transferred thereto via each inflow aperture; a plurality of valves, each connected to corresponding of the plurality of inflow apertures for controlling the suction of the leakage gas from any one inflow aperture at a time into the detector; and a controller connected to the plurality of valves for selectively opening and closing each of the plurality of valves.

In another aspect, there is provided a method for detecting leakage gas using a leakage gas detector comprising the steps of: flowing leakage gas into a plurality of inflow apertures; selectively opening and closing, by a controller, each of the plurality of valves connected to corresponding of the plurality of inflow apertures; and detecting the leakage gas transferred via each of the plurality of valves which were opened exclusively of the remaining closed valves.

Here, preferably, each of the plurality of valves is opened in sequence at a predetermined interval. In addition, the controller comprises: a program storer for storing a program by which each of the plurality of valves is selectively opened and closed; a valve controller for controlling the opening and closing of each the plurality of valves according to the program stored in the program storer; a program processor for processing the program stored in the program storer which drives the valve controller; and a program driver for driving the program.

BRIEF DESCRIPTION OF THE DRAWINGS

The above objects and advantages of the present invention will become more apparent by describing in detail a preferred embodiment thereof with reference to the attached drawings in which:

FIG. 1 is a block diagram of a leakage gas detector for a semiconductor device according to the present invention;

FIGS. 2A–2C are timing diagrams showing opening and closing signals of each valve shown in FIG. 1.

DETAILED DESCRIPTION OF THE INVENTION

Figure 3:
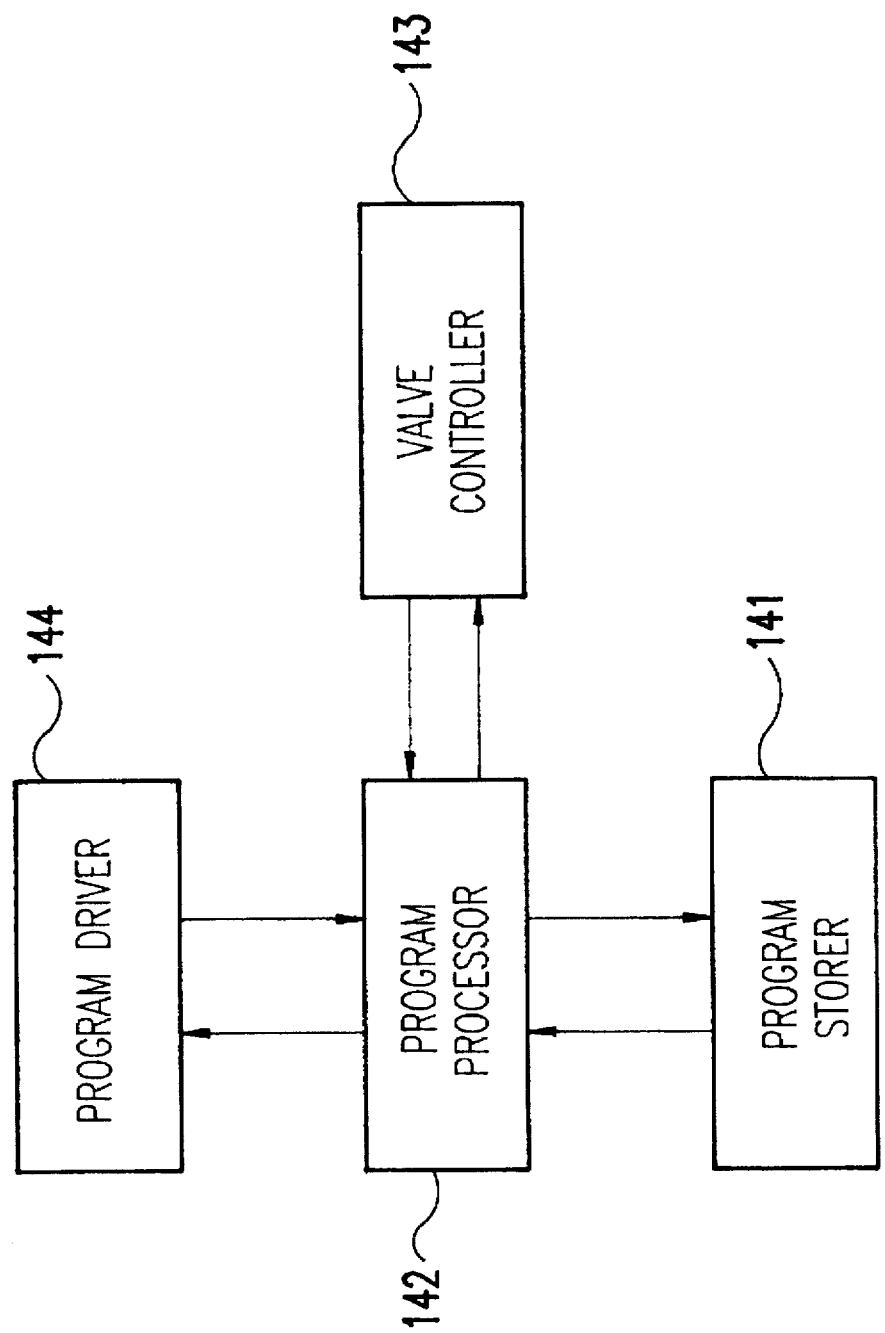
FIG. 3 is a block diagram showing the structure of the controller shown in FIG. 1.

Referring to FIG. 1, a leakage gas detector according to the present invention includes a detector 11, first, second and third inflow apertures 12a, 12b and 12c, each of which is connected to the detector 11, and into which the leakage gas flows. First, second and third valves 13a, 13b and 13c are connected to the inflow apertures 12a, 12b and 12c for controlling the inflow of the leakage gas into the detector 11. A controller 14 selectively controls the opening and closing of each valve 13a, 13b and 13c. A pump 15 is connected to the detector 11 for suctioning the leakage gas through the inflow apertures 12a, 12b and 12c. Also, the leakage gas detector of the present invention further includes an alarm 16 that is generated which terminates the operation of the reaction equipment if the amount of leakage gas is above a predetermined value.

The detector 11 can detect the amount of leakage gas flowing through each of the inflow apertures 12a, 12b and 12c.

A general air valve can be used for valves 13a, 13b and 13c. Solenoid valves 23a, 23b, and 23c are connected to the respective valves 13a, 13b and 13c. The solenoid receives a valve opening and closing signal from the controller 14 to control the opening and closing of the valves 13a, 13b and 13c.

For selectively controlling the valves 13a, 13b and 13c, a preferred embodiment of the present invention utilizes a time sharing method. According to the time sharing method, the valves 13a, 13b and 13c are opened in sequence at a predetermined interval, allowing a greater amount of the leakage gas to enter the detector 11 through the opened valve. Thus, suction pressure is increased, thereby decreasing the detection time required to sense the leakage gas in the detector 11 and improving the detection ability.

FIGS. 2A–2C are timing diagrams showing valve opening and closing signals from the controller 14, which are for opening the valves 13a, 13b and 13c in sequence according to the time sharing method. Here, intervals A, B and C together represent the summed opening time of each valve 13a, 13b and 13c. That is, the first, second and third valves 13a, 13b and 13c are opened during time intervals A, B and C, respectively. As described above, only one valve is opened during a specific interval while the remaining valves are closed, so that the applied suction pressure of the pump 15 is maximized.

FIG. 3 is a block diagram showing the structure of the controller 14 shown in FIG. 1. As shown in FIG. 3, the controller 14 is comprised of a program storer 141 for storing a valve opening and closing program. The program resides on a Read-Only-Memory (ROM) and controls the valve opening and closing signals according to the time sharing method, as shown in FIGS. 2A–2C. Controller 14 further includes a program processor 142 connected to the program storer 141. The program processor is a central processing unit (CPU) or microprocessor for processing the valve opening and closing program. A valve controller 143 is connected to the program processor 142 for controlling the mechanical or pneumatic opening and closing of the valves 13a, 13b and 13c. A program driver 144 drives the valve opening and closing program. Here, a programmable logic controller (PLC) or microcomputer may be used as the controller 14.

Referring to FIGS. 1–3, the operation of the leakage gas detector according to the present invention will now be described.

First, during interval A .shown in FIGS. 2A–2C, only the first valve 13a is opened by the controller 14 and the second and third valves 13b and 13c are closed. The program processor 142 of the controller 14 processes the valve opening and closing program from the program storer 141 to recognize that the first valve 13a should be opened during interval A and the program processor 142 then drives the valve controller 143. The first valve 13a is opened according to the driving of the valve controller 143 and the two remaining valves 13b and 13c are closed. Accordingly, the leakage gas enters the detector 11 via the first inflow aperture 12a and the first valve 13a. The detector 11 detects whether the amount of leakage gas is over a predetermined value. If the amount of the leakage gas is over the predetermined value, an alarm signal 16 is generated which terminates the operation of the reaction equipment.

Next, by continuously operating the controller 14, the program processor 142 recognizes the termination of interval A and the start of interval B. The program processor 142 drives the valve controller 143 to open the second valve 13b and simultaneously close the first valve 13a. The third valve 13c also remains closed. Thus, the leakage gas enters the detector 11 via the second inflow aperture 12b and the second valve 13b. The detector 11 performs the detecting process as described above.

In the same manner, when the program processor 142 recognizes the termination of interval B and the start of interval C, the program processor drives the valve controller 143 to open the third valve 13c and simultaneously close the second valve 13b. The first valve 13a also remains closed. Thus, the leakage gas enters the detector 11 via the third inflow aperture 12c and the third valve 13c. The detector 11 performs the detecting process as described above.

According to the present invention, three valves are selectively opened by the time sharing method, so that the suction pressure of the leakage gas increases by about 7 to 10 times compared with the conventional leakage gas detector where three valves are simultaneously opened. Thus, the amount of leakage gas entering the detector 11 within the same period is increased relatively, thereby shortening the required detection time and improving the leakage gas detection ability of the leakage gas detector.

In order to clarify the effect of the present invention, the suction pressure of the leakage gas in the conventional leakage gas detector, where three inflow apertures are simultaneously opened, and that of the present invention are compared in TABLE 1.

TABLE 1

| Inflow Apertures | Prior Art | Present Invention |
| --- | --- | --- |
| 1st | −30 mmHg | −200 mmHg |
| 2nd | −21 mmHg | −200 mmHg |
| 3rd | −20 mmHg | −200 mmHg |

As shown in TABLE 1, the suction pressure of the leakage gas through the first inflow aperture 12a is increased by about times that of the conventional leakage gas detector, and the suction pressure of the leakage gas via the second and third inflow apertures 12b and 12c is increased by about a factor of 10.

The detection ability of the conventional leakage gas detector and that of the present leakage gas detector are shown in TABLE 2.

TABLE 2

| Inflow Apertures | Prior Art | | Present Invention | |
| --- | --- | --- | --- | --- |
| | Condition 1 | Condition 2 | Condition 1 | Condition 2 |
| 1st | Undetectable | Detection after 5 minutes | Detection after 1 minute | Immediate Detection |
| 2nd | Undetectable | Detection after 9 minutes | Detection after 1 minute | Immediate Detection |
| 3rd | Undetectable | Detection after 9 minutes | Detection after 1 minute | Immediate Detection |

In TABLE 2, condition 1 corresponds to a leakage of 10 cc of Hydrogen Chloride gas (HCl) and 18 liters of $N_2$, respectively, at −25 $mmH_2O$ of suction pump discharge pressure. Condition 2 corresponds to a leakage of 15 cc of HCl and 18 liters of $N_2$ respectively, at −25 $mmH_2O$ of suction pump discharge pressure. As shown in TABLE 2, in regard to the inflow apertures, the conventional leakage gas detector cannot detect the leakage gas at all under condition 1, while the leakage gas detector of the present invention detects the leakage gas after 1 minute. Also, in condition 2, the conventional leakage gas detector detects the leakage gas after 5 or 9 minutes while the leakage gas detector of the present invention detects the leakage gas immediately.

The above-described leakage gas detector of the present invention may be used for detecting the leakage of hydrogen chloride gas (HCl) or other gases near various places in the manufacturing apparatus, including the gas injection portion of a diffusion furnace, a box of a vapor generator, and a utility box.

According to the above preferred embodiment, there are provided three inflow apertures and three corresponding valves for the convenience of description. It is understood, however, that the use of two or more inflow apertures and corresponding valves are contemplated, and are considered within the spirit and scope of this invention.

As described above, according to the leakage gas detector and the detecting method of the present invention, the leakage gas enters only one inflow aperture and valve during a specific interval, so that the suction pressure of leakage gas is increased, thereby shortening the detection time required to sense the leakage gas.

While the present invention has been illustrated and described with reference to a specific embodiment, the present invention is not limited to the particular form illustrated and further modifications and alterations that do not depart from the spirit and scope of this invention will occur to those skilled in the art.

What is claimed is:

1. A leakage gas detector for a semiconductor device comprising:

a plurality of inflow apertures into which a leakage gas may flow;

a detector for detecting the leakage gas, if any, transferred thereto via each inflow aperture;

a pump disposed downstream of said inflow apertures for drawing any of said leakage gas towards and through said detector by applying a suction pressure to any of said leakage gas emanating from said semiconductor device;

a plurality of valves, each connected to corresponding ones of said plurality of inflow apertures for increasing the suction pressure of any leakage gas flowing into said detector from said corresponding ones of said plurality of inflow apertures; and a controller connected to said plurality of valves for sequentially opening and then closing each of said plurality of valves in turn.

2. A leakage gas detector as claimed in claim 1, wherein said plurality of valves are opened and closed in sequence at a predetermined time interval.

3. A leakage gas detector as claimed in claim 1, further comprising a means for generating an alarm signal, connected to said detector, when the amount of leakage gas is above a predetermined value.

4. A leakage gas detector as claimed in claim 1, wherein said controller comprises:

a program storer for storing a program by which each of said plurality of valves is selectively opened and closed;

a valve controller for controlling the opening and closing of each said plurality of valves according to the program stored in said program storer;

a program processor for processing the program stored in said program storer which drives said valve controller; and a program driver for driving the program.

5. A leakage gas detector as claimed in claim 2, wherein said controller comprises:

a program storer for storing a program by which each of said plurality of valves is selectively opened and closed;

a valve controller for controlling the opening and closing of each said plurality of valves according to the program stored in said program storer;

a program processor for processing the program stored in said program storer which drives said valve controller; and a program driver for driving the program.

6. A leakage gas detector as claimed in claim 1, wherein the number of said plurality of inflow apertures and said plurality of valves are three, respectively.

7. A leakage gas detector as claimed in claim 1, wherein said plurality of valves are air valves.

8. A leakage gas detector as claimed in claim 7, wherein each of said plurality of valves is connected to a solenoid valve for controlling the amount of air supplied to said plurality of valves.

9. A method for detecting leakage gas using a leakage gas detector for a semiconductor device which includes a plurality of inflow apertures into which the leakage gas enters, a detector for detecting the leakage gas transferred thereto via each of said plurality of inflow apertures, a pump disposed downstream of said inflow apertures for drawing any of said leakage gas towards and through said detector by applying a suction pressure to any of said leakage gas emanating from said semiconductor device, a plurality of valves, each connected to corresponding ones of said plurality of inflow apertures for increasing the suction pressure of any leakage gas flowing into said detector from said corresponding ones of said plurality of inflow apertures, and a controller connected to said plurality of valves to open and close each of said plurality of valves, wherein said controller selectively opens each of said plurality of valves in a sequential manner so as to produce an increased suction pressure during a time interval over which each one of said plurality of valves is opened in sequence.

10. A method for detecting leakage gas using a leakage gas detector for a semiconductor device which includes a plurality of inflow apertures, a detector, a pump disposed downstream of said inflow apertures, a plurality of valves, each connected to corresponding ones of said plurality of inflow apertures for increasing the suction pressure of any leakage gas flowing into said detector from said corresponding ones of said plurality of inflow apertures, and a controller connected to said plurality of valves, the method comprising the steps of:

flowing leakage gas into said plurality of inflow apertures;

selectively opening and then closing, by the controller, each of said plurality of valves connected to the corresponding ones of said plurality of inflow apertures; and suctioning said leakage gas during a time interval over which each one of said plurality of valves is opened in a sequential manner from open ones of each of said plurality of inflow apertures towards and through said detector with said pump;

detecting the leakage gas transferred via each of said plurality of valves which were opened.

11. A method for detecting leakage gas as claimed in claim 10, wherein during said opening and closing step, each of said plurality of valves is opened and closed in sequence at a predetermined time interval.

12. A method for detecting leakage gas as claimed in claim 10, further comprising the step of generating an alarm signal when the amount of leakage gas is above a predetermined value.

13. A method for detecting leakage gas as claimed in claim 10, wherein said opening and closing step comprises the sub-steps of:

storing a program, in a program storer, by which each of said plurality of valves is selectively opened and closed;

controlling the opening and closing of each of said plurality of valves according to the program stored in said program storer;

processing the program stored in said program storer which drives said valve controller; and driving the program.

14. A method for detecting leakage gas as claimed in claim 11, wherein said opening and closing step comprises the sub-steps of:

storing a program, in a program storer, by which each of said plurality of valves is selectively opened and closed;

controlling the opening and closing of each of said plurality of valves according to the program stored in said program storer;

processing the program stored in said program storer which drives said valve controller; and driving the program.

15. A method for detecting leakage gas as claimed in claim 10, wherein the flowing, opening and closing, and detecting steps utilize three inflow apertures and three valves.

16. A method for detecting leakage gas as claimed in claim 10, wherein the plurality of valves in the flowing, opening and closing, and detecting steps, are air valves.

17. A method for detecting leakage gas as claimed in claim 16, wherein said opening and closing step utilizes a plurality of solenoid valves, each connecting to corresponding of the plurality of valves, for controlling the amount of air supplied to said valves.

* * * * *